United States Patent [19]

Applezweig

[11] Patent Number: 4,680,289

[45] Date of Patent: Jul. 14, 1987

[54] TREATMENT OF OBESITY AND DIABETES USING SAPOGENINS

[75] Inventor: Norman Applezweig, New York, N.Y.

[73] Assignee: Progenics, Inc., New York, N.Y.

[21] Appl. No.: 741,534

[22] Filed: Jun. 5, 1985

[51] Int. Cl.$^4$ .................. A61K 31/58; C07J 71/00
[52] U.S. Cl. ................................ 514/172; 540/17; 426/2
[58] Field of Search ............. 514/172; 260/239.55 A; 426/2; 540/17

[56] References Cited

PUBLICATIONS

Merck Index (1976) pp. 439 and 1106.
Fieser et al., "Steroids", (1959) p. 831.

*Primary Examiner*—Leonard Schenkman
*Assistant Examiner*—Joseph A. Lipovsky
*Attorney, Agent, or Firm*—Ostrolenk, Faber, Gerb & Soffen

[57] ABSTRACT

Obesity and diabetes obesity syndromes are treated with 5$\beta$-sapogenin or $\Delta^5$ sapogenin.

24 Claims, No Drawings

TREATMENT OF OBESITY AND DIABETES USING SAPOGENINS

CROSS-REFERENCE TO RELATED APPLICATION

This invention is related to U.S. patent application Ser. No. 683,423, filed Dec. 19, 1984 for Treatment of Obesity, Diabetes and Other Symptoms of Hypercorticoidism Using Etiocholanolones, and to U.S. patent application Ser. No. 515,354, filed on July 19, 1983 for "Method for Treating Diabetes Using DHEA Components" and the contents of these applications are incorporated herein by reference.

BACKGROUND OF THE INVENTION

The major function of the adrenal gland is to regulate metabolism in the body so that an intermittent intake of food can be regulated to maintain a constant metabolite supply to the cells. This is accomplished by producing steroid hormones which can control the conversion of incoming nutrients, such as aminoacids, glucose and fats into storage depots from which they can thereafter be released or interchanged, allowing a continuous flow of optimum energy and growth factors to the cells.

One category of steroids is known as the adrenal androgens. Dehydroepiandrosterone (DHEA) is the principal representative of this category. The adrenal androgens which have an anabolic action are produced with puberty, reach a peak in early adulthood and then, beyond the age of 50, decline to very low levels.

When the body is subjected to stress, physical or mental, e.g. injury, cold, starvation or threats, real or imagined, the adrenal cortico-trophic hormone (ACTH), which is secreted by the pituitary gland, stimulates the adrenal cortex to produce steroids in increased amounts in order to provide the body with resources necessary for response to the stress, storage or release of glucose when needed, lipid deposition or mobilization in order to maintain the energy equilibrium of the body under conditions where extra energy may be needed and/or starvation of the cells becomes a possibility.

Under normal conditions, ACTH stimulates the adrenals to secrete DHEA as well as cortisol in younger persons. In the aging individual, secretion of cortisol continues but that of DHEA declines, thus leading to a relative hypercortisolism which can result in obesity, diabetes and decrease in immune function.

DHEA is metabolized in the body. A major metabolite is etiocholanolone (5-$\beta$-androstan-3-$\alpha$-ol-17-one, (hereinafter referred to as $\alpha$-ET) and in normal individuals it is excreted in amounts of about 0.5 mg/100 ml. $\beta$-etiocholanolone (5-$\beta$-androstan-3-$\beta$-ol-17-one, hereinafter referred to as $\beta$-ET), was reported to be a minor metabolite of DHEA although evidence for its presence was based upon unmeasured spots on chromatograph strips observed during measurements of etiocholanolone excretion. Even when large quantities of $\beta$-ET are ingested, most of the recovered excretion product is in the form of $\alpha$-ET, with less than 5% of $\beta$-ET found. Kappas, et al, *The Thermogenic Effect and Metabolite Fate of Etiocholanolone in Man*, J. Clin. Endocrin. & Metab., 18, 1043–1055 (1958). It is shown in said related application Ser. No. 683,423, that the administration of $\alpha$-ET, $\beta$-ET or mixtures thereof reproduced the effects of DHEA in preventing the development of hyperglycemia and diabetes. It was also discovere that the effective therapeutic amounts of these compounds are considerably lower than the dosage of DHEA required for maximum effect in normalizing blood sugar and maintaining islet integrity. It has further been found that these compounds are superior anti-obesity agents compared to DHEA.

Two additional metabolites of DHEA are androsterone and epiandrosterone. Both of these compounds are 5-$\alpha$ isomers and unlike the etiocholanolones are androgenic and show no anti-obesity or anti-hyperglycemic actions.

It is shown in the aforesaid related application Ser. No. 683,423 that the etiocholanolones are useful in the treatment of diabetes in mutant mice and treatment of adult-onset diabetes in obese individuals. DHEA and etiocholanolones are also known to be useful as an anti-obesity agent in animals and humans. Yen et al, Prevention of Obesity in Avy/a Mice by Dehydroepiandrosterone, Lipids, 12(5), 409 (1977); Kritchevsky et al, Influence of Dehydroepiandrosterone (DHEA) Cholesterol Metabolism in Rats, Pharm. Res. Comm., 15, No. 9 (1983); Abrahamsson et al, Catabolic Effects and the Influence on Hormonal Variables under Treatment with Gynodian-Depot or Dehydroepiandrosterone (DHEA) Oenanthate, Maturitas, 3 (1981) 225-234.

It has now been discovered that the administration of 5-$\beta$ sapogenin chemical precursors of $\alpha$-ET and $\beta$-ET are useful in preventing the development of obesity, hyperglycemia and diabetes. If the 5 position is unsaturated, then the body reduces it to a mixture of 5-$\alpha$ and 5-$\beta$ and it has about one-half the activity of the 5-$\beta$ sapogenins. The 5-$\alpha$ sapogenins are not effective in preventing the development of hyperglycemia and diabetes.

It is accordingly the object of this invention to provide a new method for treating obesity, diabetes-obesity syndrome and enhancing the function or by preventing the destruction of the pancreatic islet beta cells using 5-$\beta$ sapogenins as anti-obesity, antidiabetic and antihyperglycemic agents. This and other objects of the invention will become apparent to those skilled in this art from the following description.

SUMMARY OF THE INVENTION

This invention relates to the treatment of obesity, diabetes-obesity syndromes and resulting hypercorticoidism through the administration of 5-$\beta$ sapogenins or $\Delta^5$ sapogenin.

DESCRIPTION OF THE INVENTION

In accordance with the present invention, 5-$\beta$ sapogenins are administered to an individual in order to treat various hyperactivity syndromes particularly obesity, and diabetes. The 5-$\beta$ sapogenins are administered orally or parentally. The usual array of oral or parental dosage forms can be used, for example, tablets can be prepared by combining one or more 5-$\beta$ sapogenins with the conventionally used binders and excipients. If desired, the compounds can be administered in a finely dispersed form, for example, as a finely dispersed powder or solution which is typically mixed with the food diet. In general, the administration amount to an average 70 kilo individual will be about 25 to 2,000 mg. per day and preferably about 100 to 800 mg. Unit dosage administration forms will generally contain about 25–1,000 mg., preferably about 50–400 mg., of the compounds. When combined with the diet, the compounds are usually used in an amount of up to about 1 percent by weight thereof. The compounds can be dissolved in a suitable solvent such as acetone, which is then mixed with food and thereafter the solvent is evaporated to leave the compounds in finely dispersed powdered form thoroughly mixed throughout the food.

The active compounds of the present invention are sapogenins which are chemical precursors of etiocholanolones. The 5 position of such sapogenins may be unsaturated as exemplified by diosgenin (nitogenin; (25R)-spirostan-5-en-3β-ol), a compound of the formula

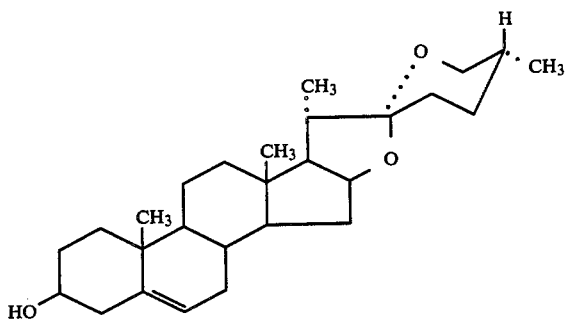

which is a known chemical precursor of DHEA and can be converted to a mixture of its cis and trans metabolites by the body. The 5 position can also be saturated as exemplified by sarsasapogenin (parigenin; (25S)-spirostan-3β-ol) with a 5-β configuration

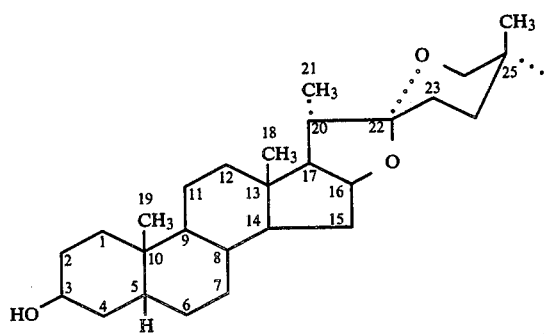

or its C25 isomer smilagenin (isosarsasapogenin; (25R)-sprirostan-3β-ol)

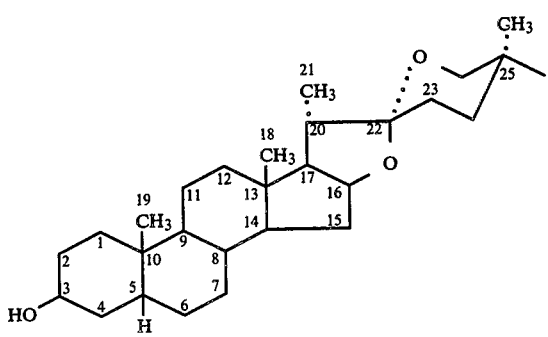

which yield only the cis isomer of DHEA, i.e. 3β-ET. The 5-α sapogenins such as tigogenin, which give rise only to 5-α trans isomers have been found to be ineffective. The activity of the 5-β or 5 saturated sapogenins are, in general, related to the relative percent of the cis isomer that can be anticipated as a result of their metabolic conversion. Thus, sarsasapogenin and smilagenin which give rise only to the cis isomer β-ET are more active than diosgenin which gives rise to both cis and trans metabolites. It should be noted that diosgenin and tigogenin have previously been used for reducing blood cholesterol as shown, for example, in Cayen et al, U.S. Pat. No. 3,890,438.

The efficacy of the 5-β sapogenins have been demonstrated in experiments with mice with diabetes-obesity condition produced by mutant diabetes (db) gene. The severity of the diabetes depends on the background genetic factors inherent in the inbred strains in which the mutations are maintained and expressed. The mice used were C57BL/Ks-db/db mice obtained from the Jackson Laboratory of Bar Harbor, Maine. In these mice, the diabetes mutation elicits an exaggerated obesity and a severe life-shortening diabetes. This diabetes is characterized by hyperplasia and hypertrophy of the beta cells of the islets of Langerhans, followed by severe degranulation and subsequent atrophy of the islets, rising blood glucose concentrations over 400 mg/dl, and death at 5-8 months.

Male mice were used. The mice were divided into groups, one of which was fed chow alone (Old Guilford 96) and others fed the chow into which either smilagenin, diosgenin, sarsasapogenin or tigogenin had been incorporated. Incorporation was effected by dissolving the compounds in acetone which was mixed with the food diet, followed by evaporation of the acetone prior to use.

The mice were weighed weekly at the time of bleeding for determination of the blood sugar concentration. Blood glucose tests were carried out as described in Coleman, et al, Studies with the Mutation, Diabetes, in the Mouse, Diabetologia 3: 238-248 (1967).

The following Table I sets forth the effects of the tests on the diabetes syndrome in the mice which had been studied for up to 16 weeks after weaning.

TABLE I

| Compound | % in Diet | Weeks | Blood Sugar mg/dl Treated | Control |
| --- | --- | --- | --- | --- |
| Similagenin | 0.4 | 16 | 111 | >400 |
| Diosgenin | 0.4 | 8 | 196 | >400 |
| Sarsasapogenin | 0.4 | 16 | 115 | >400 |
| Tigogenin | 0.8 | 10 | >400 | >400 |

Table II sets forth the results of the weight gain experiments using C57BL/6 mice:

TABLE II

| Compound | % in Diet | Weeks | % Change From Start Weight Treated | Control |
| --- | --- | --- | --- | --- |
| Sarsasapogenin | 0.4 | 4 | 45.1 | 83.1 |
| Diosgenin | 0.4 | 4 | 38.5 | 83.1 |
| Smilagenin | 0.4 | 4 | 45.8 | 83.4 |
| Tigogenin | 0.8 | 10 | No Effect | |

The effects of these compounds, while beneficial, are believed to be reversible by cessation of administration of the compounds. Furthermore, intervention with the treatment of the present invention has beneficial effects when introduced during any stage except the terminal stage of the diabetic cycle. The cycle is typically characterized by hyperactivity of the pancreas and hyperinsulinism followed by degeneration, then atrophy of the beta cells of the islet of Langerhans. Intervention at the early stages according to the present invention can actually avert the degeneration and atrophy, maintaining the islets in healthy condition despite continuing hyperactivity. Intervention at the later stages may reverse the process resulting in regeneration and enhancement of residual beta cell function.

In mutants carrying the mutation (db/db), the most obvious effects observed depend on the severity of the diabetes which depends on the inbred strain in which the mutant is maintained. Thus, the invention compounds in the C57BL/Ks mutant palliate the diabetes and have only a minor effect on rate of weight gain. In contrast, diabetes mutants maintained on the C57BL/6 inbred background are characterized by a mild diabetes associated with severe obesity. On this strain, the beneficial effects of the compounds involve, primarily, the rate of weight gain (Table II). Even so, the decrease in weight gain observed is significant and the mutants still remain substantially healthy, non-obese and free of diabetes symptoms.

These results set forth above clearly document the efficacy of the compounds of this invention with respect to their ability to treat diabetes, prevent obesity and control established obesity without any obvious detrimental consequences.

A typical capsule which can be prepared according to this invention will contain 50 mg. smilagenin, 50 mg. lactose, 50 mg. dicalcium phosphate, 2 mg. magnesium stearate and 10 mg. of talc. Typical tablets can contain 50 mg. sarsasapogenin, 150 mg. starch, 5 mg. magnesium stearate, 10 mg. stearic acid and 40 mg. of dicalcium phosphate, or 50 mg. sarsasapogenin, 50 mg. smilagenin, 150 mg. starch, 5 mg. magnesium stearate, 10 mg. stearic acid and 40 mg. of dicalcium phosphate.

A typical parental formulation is 10 mg of smilagenin and 30 mg. of glycine as sterile solids in an ampoule. Just before use, the ampoule contents are mixed with 3 ml of propylene glycol (or other diluent).

Various changes and modifications can be made in the method of the present invention without departing from the spirit and scope thereof. The various embodiments which have been described herein were for the purpose of further illustrating the invention but were not intended to limit it. Unless other otherwise specified, all temperatures are in degrees Centigrade and all parts and percentages are by weight throughout this specification and claims.

What is claimed is:

1. A method of treating a condition selected from the group consisting of obesity and diabetes syndromes which comprises administering to a mammal an obesity or diabetes antagonizing effectuve amount of a $5\beta$-sapogenin or a $\Delta^5$ sapogenin.

2. The method of claim 1, wherein the administration is oral or parental.

3. The method of claim 2, wherein said sapogenin is diosgenin.

4. The method of claim 2, wherein said sapogenin is smilagenin or sarsasapogenin.

5. The method of claim 1, wherein the amount administered is about 25–2,000 mg. per 70 kilos.

6. The method of claim 5, wherein the amount is about 100–800 mg.

7. The method of claim 1, wherein said sapogenin is administered in combination with food.

8. The method of claim 7, wherein said sapogenin is present in an amount up to about 1% of said food.

9. The method of claim 7, wherein said sapogenin is in finely dispersed powdered form.

10. The method of claim 1, wherein said sapogenin is in finely dispersed powdered form.

11. A method of treating obesity comprising administering to a mammal an obesity antagonizing effective amount of a $5\beta$-sapogenin or a $\Delta^5$ sapogenin.

12. The method of claim 11, wherein said sapogenin is diosgenin.

13. The method of claim 11, wherein said sapogenin is smilagenin or sarsasapogenin.

14. The method of claim 11, wherein the amount administered is about 25–2,000 mg. per 70 kilos.

15. The method of claim 14, wherein the amount is 100–800 mg.

16. A composition for the treatment of a condition selected from the group consisting of obesity and diabetes syndromes comprising in combination, food and an obesity or diabetes antagonizing effective amount of a $5\beta$-sapogenin or a $\Delta^5$ sapogenin.

17. The composition of claim 16, wherein said sapogenin is diosgenin.

18. The composition of claim 16, wherein said sapogenin is smilagenin or sarsasapogenin.

19. The composition of claim 16, wherein said sapogenin is present in an amount up to about 1% of said food.

20. A method of treating diabetes syndromes which comprises administering to a mammal a diabetes antagonizing effective amount of $5\beta$-sapogenin or $\Delta^5$ sapogenin.

21. The method of claim 20, wherein said sapogenin is diosgenin.

22. The method of claim 20, wherein said sapogenin is smilagenin or sarsasapogenin.

23. The method of claim 20, wherein the amount administered is about 25–2,000 mg. per 70 kilos.

24. The method of claim 23, wherein the amount is 100–800 mg.

* * * * *